United States Patent [19]

DeFilippi

[11] 4,229,536
[45] Oct. 21, 1980

[54] PROCESS FOR PREPARING IMMOBILIZED ENZYMES

[75] Inventor: Louis J. DeFilippi, Arlington Heights, Ill.

[73] Assignee: UOP Inc., Des Plaines, Ill.

[21] Appl. No.: 974,198

[22] Filed: Dec. 28, 1978

[51] Int. Cl.³ .................. C12N 11/14; C12N 11/08; C12N 11/06
[52] U.S. Cl. .................. 435/176; 435/180; 435/181
[58] Field of Search ............ 435/176, 180, 181, 174

[56] References Cited

U.S. PATENT DOCUMENTS

| | | | |
|---|---|---|---|
| 3,519,538 | 7/1970 | Messing et al. | 435/176 |
| 3,669,841 | 6/1972 | Miller | 435/176 |
| 3,705,084 | 12/1972 | Reynolds | 435/180 |
| 3,715,278 | 2/1973 | Miller | 435/181 X |
| 3,783,101 | 1/1974 | Tomb et al. | 435/176 |
| 3,796,634 | 3/1974 | Haynes et al. | 435/180 |
| 3,802,997 | 4/1974 | Messing | 435/176 |
| 3,821,083 | 6/1974 | Van Leemputten et al. | 435/176 |
| 3,930,950 | 1/1974 | Royer | 435/176 |
| 4,071,409 | 1/1978 | Messing et al. | 435/176 |
| 4,072,566 | 2/1978 | Lynn | 435/176 |

*Primary Examiner*—David M. Naff
*Attorney, Agent, or Firm*—James R. Hoatson, Jr.; Raymond H. Nelson; William H. Page, II

[57] ABSTRACT

The activity and stability of immobilized enzymes may be improved by treating an immobilized enzyme comprising an enzyme covalently bound to polymeric material which is absorbed on an inorganic porous support material with a bifunctional monomeric material and a substrate followed by additional treatment with an enzyme and thereafter again treating the complex with additional bifunctional monomer and substrate.

15 Claims, No Drawings

PROCESS FOR PREPARING IMMOBILIZED ENZYMES

BACKGROUND OF THE INVENTION

It is known that enzymes, which are proteinaceous in nature and which are commonly water soluble or capable of being solubilized, comprise biological catalysts which serve to regulate many and varied chemical reactions which occur in living organisms. The enzymes may also be isolated and used in analytical, medical and industrial applications. For example, they find use in industrial applications in the preparation of food products such as cheese or bread as well as being used in the preparation of alcoholic beverages. Some specific uses in industry may be found in the use of enzymes such as in the resolution of amino acids; in the modification of penicillin to form various substrates thereof; the use of various proteases in cheese making, meat tenderizing, detergent formulations, leather manufacture and as digestive aids; the use of carbohydrases in starch hydrolysis, sucrose inversion, glucose isomerization, etc.; the use of nucleases in flavor control; or the use of oxidases in oxidation prevention and in the color control of food products. These uses as well as many others have been well delineated in the literature.

As hereinbefore set forth, inasmuch as enzymes are commonly water soluble as well as being generally unstable and readily deactivated, they are also difficult either to remove from the solutions in which they are utilized for subsequent reuse or it is difficult to maintain their catalytic activity for a relatively extended period of time. The aforementioned difficulties will, of course, lead to an increase cost in the use of enzymes for commercial purposes due to the necessity for frequency replacement of the enzyme, this replacement being usually necessary with each application. To counteract the high cost of replacement, it has been suggested to immobilize or insolubilize the enzymes prior to the use thereof. By immobilizing the enzymes through various systems hereinafter set forth in greater detail, it is possible to stabilize the enzymes in a relative manner and, therefore, to permit the reuse of the enzyme which may otherwise undergo deactivation or be lost in the reaction medium. Such immobilized or insolubilized enzymes may be employed in various reactor systems such as in packed columns, stirred tank reactors, etc., depending upon the nature of the substrate which is utilized therein. In general, the immobilization of the enzymes provides a more favorable or broader environmental and structural stability, a minimum of effluent problems and materials handling as well as the possibility of upgrading the activity of the enzyme itself.

As hereinbefore set forth, several general methods, as well as many modifications thereof, have been described by which the immobilization of enzymes may be effected. One general method is to adsorb the enzyme at a solid surface as, for example, when an enzyme such as amino acid acylase is adsorbed on a cellulosic derivative such as DEAE-cellulose; papain or ribonuclease is adsorbed on porous glass; catalase is adsorbed on charcoal; trypsin is adsorbed on quartz glass or cellulose, chymotrypsin is adsorbed on kaolinite, etc. Another general method is to trap an enzyme in a gel lattice such as glucose oxidase, urease, papain, etc., being entrapped in a polyacrylamide gel; acetyl cholinesterase being entrapped in a starch gel or a silicone polymer; glutamic-pyruvic transaminase being entrapped in a polyamide or cellulose acetate gel, etc. A further general method is a cross-linking by means of bifunctional reagents and may be effected in combination with either of the aforementioned general methods of immobilization. When utilizing this method, bifunctional or polyfunctional reagents which may induce intermolecular cross-linking will covalently bind the enzymes to each other as well as on a solid support. This method may be exemplified by the use of glutaraldehyde or bisdiazobenzidine-2,2'-disulfonic acid to bind an enzyme such as papain on a solid support, etc. A still further method of immobilizing an enzyme comprises the method of a covalent binding in which enzymes such as glucoamylase, trypsin, papain, pronase, amylase, glucose oxidase, pepsin, rennin, fungal protease, lactase, etc., are immobilized by covalent attachment to a polymeric material which is attached by various means to an organic or inorganic solid porous support. This method may also be combined with the aforesaid immobilization procedures.

The above enumerated methods of immobilizing enzymes all possess some drawbacks which detract from their use in industrial processes. For example, when an enzyme is directly adsorbed on the surface of a support, the binding forces which result between the enzyme and the carrier support are often quite weak, although some prior art has indicated that relatively stable conjugates of this type have been obtained when the pore size of the support and the spin diameter of the enzyme are correlated. However, in such cases it is specified that the pore size of the support cannot exceed a diameter of about 1000 Angstroms. In view of this weak bond, the enzyme is often readily desorbed in the presence of solutions of the substrate being processed. In addition to this, the enzyme may be partially or extensively deactivated due to its lack of mobility or due to interaction between the support and the active site of the enzyme. Another process which may be employed is the entrapment of enzymes in gel lattices which can be effected by polymerizing an aqueous solution or emulsion containing the monomeric form of the polymer and the enzyme or by incorporating the enzyme into the preformed polymer by various techniques, often in the presence of a cross-linking agent. While this method of immobilizing enzymes has an advantage in that the reaction conditions utilized to effect the entrapment are usually mild so that often there is little alteration or deactivation of the enzyme, it also has disadvantages in that the conjugate has poor mechanical strength, which results in compacting when used in columns in continuous flow systems, with a concomitant plugging of the column. Such systems also have rather wide variations in pore size thus leading to some pore sizes which are large enough to permit the loss of enzyme. In addition, some pore sizes may be sufficiently small so that large diffusional barriers to the transport of the substrate and product will lead to reaction retardation, this being especially true when using a high molecular weight substrate. The disadvantages which are present when immobilizing an enzyme by intermolecular cross-linkage, as already noted, are due to the lack of mobility with resulting deactivation because of inability of the enzyme to assume the natural configuration necessary for maximum activity, particularly when the active site is involved in the binding process.

Covalent binding methods have found wide applications and may be used either as the sole immobilization technique or as an integral part of many of the methods already described in which cross-linking reactions are employed. This method is often used to bind the enzyme as well as the support through a bifunctional intermediary molecule in which the functional groups of the molecule, such as, for example, gamma-aminopropyltriethoxysilane, are capable of reacting with functional moieties present in both the enzyme and either an organic or inorganic porous support. A wide variety of reagents and supports has been employed in this manner and the method has the advantage of providing strong covalent bonds throughout the conjugate product as well as great activity in many cases. The covalent linkage of the enzyme to the carrier must be accomplished through functional groups on the enzyme which are non-essential for its catalytic activity such as free amino groups, carboxyl groups, hydroxyl groups, phenolic groups, sulfhydryl groups, etc. These functional groups will also react with a wide variety of other functional groups such as an aldehydo, isocyanato, acyl, diazo, azido, anhydro activated ester, etc., to produce covalent bonds. Nevertheless, this method also often has many disadvantages involving costly reactants and solvents, as well as specialized and costly porous supports and cumbersome multi-step procedures, which render the method of preparation uneconomical for commercial application.

The prior art is therefore replete with various methods for immobilizing enzymes which, however, in various ways fail to meet the requirements of economical industrial use. However, as will hereinafter be discussed in greater detail, none of the prior art compositions comprise the composition of matter of the present invention which constitutes an inorganic porous support containing a copolymer, formed in situ from a polyfunctional monomer, a low molecular weight polymer, a polymer hydrolysate, or a preformed polymer, of natural or synthetic origin by reaction with a bifunctional monomer, which is entrapped and also adsorbed in part within the pores of said support, and which contains terminally functionalized, pendent groups extending therefrom; the enzyme being covalently bound to the active moieties at the terminal reactive portions of the pendent groups, thus permitting the freedom of movement which will enable the enzyme to exercise maximum activity. A variable portion of the enzyme will also be adsorbed upon the matrix, but this will be recognized as an unavoidable consequence of almost all immobilization procedures involving porous inorganic supports and is not to be considered a crucial aspect of this invention. Furthermore, the bond between the inorganic support and the organic copolymer which has been prepared in situ in the pores of the support is not covalent but rather physico-chemical and mechanical in nature and the inorganic-organic matrix so produced presents high stability and resistance to disruption. As further examples of prior art, U.S. Pat. No. 3,556,945 relates to enzyme composites in which the enzyme is adsorbed directly to an inorganic carrier such as glass. U.S. Pat. No. 3,519,538 is concerned with enzyme composites in which the enzymes are chemically coupled by means of an intermediary silane coupling agent to an inorganic carrier. In similar fashion, U.S. Pat. No. 3,783,101 also utilizes an organosilane composite as a binding agent, the enzyme being covalently coupled to a glass carrier by means of an intermediate silane coupling agent, the silicon portion of the coupling agent being attached to the carrier while the organic portion of the coupling agent is coupled to the enzyme, the composition containing a metal oxide on the surface of the carrier disposed between the carrier and the silicon portion of the coupling agent. In U.S. Pat. No. 3,821,083 a water-insoluble polymer such as polyacrolein is deposited on an inorganic carrier and an enzyme is then covalently linked to the aldehyde groups of the polymer. However, according to most of the examples set forth in this patent, it is necessary to first hydrolyze the composite prior to the deposition of the enzyme on the polymer. Additionally the product which is obtained by the method of this patent suffers a number of disadvantages in that it first requires either the deposition, or initially the formation, of the desired polymer in an organic medium followed by its deposition on the inorganic carrier with a subsequent clean-up operation involving distillation to remove the organic medium. In addition to this, in another method set forth in this reference, an additional hydrolytic reaction is required in order to release the aldehyde groups from the initial acetal configuration in which they occurred in the polymer. Inasmuch as these aldehyde moieties are attached directly to the backbone of the polymer, the enzyme is also held adjacent to the surface of the polymer inasmuch as it is separated from the surface of the polymer by only one carbon atom of the reacting aldehyde group and, therefore, the enzyme is obviously subjected to the physico-chemical influences of the polymer as well as being relatively immobilized and inhibited from assuming its optimum configuration. Another prior art patent, namely, U.S. Pat. No. 3,705,084 discloses a macroporous enzyme reactor in which an enzyme is adsorbed on the polymeric surface of a macroporous reactor core and thereafter is cross-linked in place. By cross-linking the enzymes on the polymeric surface after adsorption thereof, the enzyme is further immobilized in part and cannot act freely as in its native state as a catalyst. The cross-linkage of enzymes in effect links them together, thereby preventing a free movement of the enzyme and decreases the mobility of the enzyme which is a necessary prerequisite for maximum activity.

U.S. Pat. No. 3,654,003 discloses a water-soluble enzyme conjugate which is prepared from an organic water-soluble support to which the enzyme is cross-linked and whose utility is limited only to cleaning compositions and pharmaceutical ointments. However, this enzyme composition also suffers from the disadvantages of the close proximity and interlocking of the enzyme and support, as well as the poor mechanical strength which is generally exhibited by enzyme conjugates based on organic polymeric supports.

U.S. Pat. No. 3,796,634 also discloses an immobilized biologically active enzyme which differs to a considerable degree from the immobilized enzyme conjugates of the present invention. The enzyme conjugate of this patent consists of an inorganic support comprising colloidal particles possessing a particle size of from 50 to 20,000 Angstroms with a polyethyleneimine, the latter being cross-linked with glutaraldehyde to staple the cross-linked polymer so formed as a monolayer on the surface of the colloidal particles, followed by adsorption of the enzyme directly onto this monolayer. Following this, the enzyme which is adsorbed as a monolayer on the surface of the colloidal particles is then cross-linked with additional glutaraldehyde to other adsorbed enzyme molecules to prevent them from being readily desorbed while in use. There is no indication of any covalent binding between enzyme and polymer matrix as is present in the present invention. By the enzyme molecules being cross-linked together on the surface of the support, this conjugate, therefore, is subjected to deactivation by both the cross-linking reaction and by the electronic and steric effects of the surface, said enzyme possessing limited mobility. Inasmuch as the product of this patent is colloidal in nature, it also possesses a very limited utility for scale-up to commercial operation, since it cannot be used in a continuous flow system such as a packed column because it would either be carried along and out of the system in the flowing liquid stream or, if a restraining membrane should be employed, the particles would soon become packed against the barrier to form an impervious layer. In addition, such a colloidal product could not readily be utilized in a fluidized bed apparatus, thereby limiting the chief utility to a batch type reactor such as a stirred tank type reactor from which it would have to be separated by centrifugation upon each use cycle. In contrast to this, the immobilized enzyme conjugates of the present invention may be employed in a wide variety of batch or continuous type reactors and therefore are much more versatile with regard to their modes of application.

In addition, another prior art reference U.S. Pat. No. 3,959,080 relates to a carrier matrix for immobilizing biochemical effective substances. However, the matrix which is produced according to this reference constitutes the product derived from the reaction of an organic polymer containing cross-linkable acid hydrazide or acid azide groups with a bifunctional cross-linking agent such as glutaraldehyde. However, this matrix also suffers from the relatively poor mechanical stability and other deficiencies which are characteristic of organic enzyme supports as well as the relatively complex organic reactions employed in preparing such polymeric hydrazides, etc.

As will hereinafter be shown in greater detail by utilizing the process of the present invention, it is possible to improve both the long term stability and total activity of immobilized enzymes.

This invention relates to a method for improving both the long term stability and total activity of immobilized enzyme complexes. More specifically, the invention is concerned with the process whereby an immobilized enzyme may be subjected to additional steps in a process to thereby enhance the desired characteristics of the complex. The immobilized enzyme complex will comprise a support matrix which consists of a combined inorganic-organic composite in which the organic porous support material contains an organic copolymer which has been formed in situ from the reaction between a first monomer with an excess of a second bifunctional monomeric material containing suitable reactive moieties. The organic copolymeric material which forms one component of the support matrix is both entrapped and also absorbed in part in the pores of the aforesaid porous support material and is further provided with functionalized pendant groups being located at the terminal portions thereof due to the use of sufficient excess of the bifunctional monomeric material. This support material or matrix may be used as the support for immobilizing an enzyme which is covalently bound to the aforesaid functionalized pendent groups at the terminal reactive portions thereof.

As hereinbefore set forth, the use of enzymes in analytical, medical or industrial applications may be greatly enhanced if said enzymes are in an immobilized condition, that is, said enzymes, by being in combination with other solid materials, are themselves in such a condition whereby they are not water soluble and therefore they may be subjected to repeated use while maintaining the catalytic activity of said enzyme. In order to be present in an immobilized state, the enzymes must be bound in some manner to a water insoluble carrier, therey being commercially usable in an aqueous insoluble state.

It is therefore an object of this invention to provide a process for preparing immobilized enzyme complexes.

A further object of this invention is to provide a process for preparing immobilized enzyme complexes which possess desirable characteristics pertaining to stability and total activity.

In one aspect an embodiment of this invention resides in a process for increasing the activity and stability of an immobilized enzyme which comprises the steps of treating an inorganic porous support material which possesses pore diameter of from about 100 to about 55,000 Angstroms and a surface area of from about 1 to about 500 $m^2/g$ with a solution of a first water soluble bifunctional monomer, removing unabsorbed monomer, contacting the treated support material with a solution containing an excess of a second bifunctional monomeric material wherein said second bifunctional monomeric material reacts with said first monomer absorbed on said support material to form a polymeric material, removing unreacted second bifunctional monomeric material, treating the resultant inorganic-organic support matrix with an enzyme to covalently bind said enzyme to said support matrix, treating the resultant enzyme-support matrix complex with an additional amount of said second bifunctional monomeric material plus substrate if desired, removing excess bifunctional monomeric material, treating said complex with an additional amount of enzyme, removing excess substrate and enzyme, and treating said complex with a mixture of substrate if desired and bifunctional monomeric material, all processes being performed at a temperature in the range of from about 0° to about 20° C.

A specific embodiment of this invention is found in a process for increasing the activity and stability of an immobilized enzyme which comprises the steps of treating gamma-alumina with an aqueous solution of polyethyleneimine, removing unabsorbed polyethyleneimine, contacting the treated alumina with an aqueous solution of glutaraldehyde which is present in an excess of from about 2 to 50 or more moles of glutaralydehyde per mole of polyethyleneimine, removing excess glutaraldehyde, treating the resultant inorganic-organic support matrix with glucose isomerase to covalently bind said glucose isomerase to said support matrix, treating said complex with an additional amount of glutaralydehyde and removing any excess glutaraldehyde, adding fructose if desired to the complex at a temperature in the range of from about 0° to about 20° C., treating said complex with an additional amount of glucose isomerase, removing excess fructose and glucose isomerase and treating the complex with a mixture of fructose and glutaralydehyde.

Other objects and embodiments will be found in the following detailed description of the present invention.

As hereinbefore set forth the present invention is concerned with a process for increasing the long term stability and total activity of immobilized enzymes. The immobilized enzymes comprise a combined inorganic-organic material consisting of an inorganic porous support material of a type hereinafter set forth in greater detail containing a copolymeric organic material which is both entrapped and also absorbed in part in the pores of said inorganic porous support. In addition, the copolymeric organic material will also contain pendent groups extending therefrom, said pendent groups containing terminally positioned functional moieties which will enable an enzyme to be covalently bound to said groups at the reactive terminal portions thereof. In contradistinction to other compositions of matter as set forth in the prior art, the support matrix of this invention, by virtue of its particular configuration, will enable the enzyme to be immobilized thereon whereby the mechanical strength and stability of the enzyme conjugates or complexes which result from this covalent binding of the enzymes to the support matrixes will be greater than that which is possesed by the immobilized enzymes of the prior art.

The process of the present invention may be effected in a relatively simple manner. In the preferred method of preparation the inorganic support material will be treated with a solution, preferably aqueous in nature, of a first monomer, following which the unabsorbed solution is removed by any means known in the art such as treating, etc. While the preferred solution is aqueous in nature, it is also contemplated within the scope of this invention that other inexpensive organic solvents such as acetone, methanol, tetrahydrofuran, etc., may also be used as the carrier for the aforementioned initially added monomer. Following the removal of the unabsorbed solution and washing with water, the wet porous support is then contacted with a sufficiently large excess of a second bifunctional monomer, said excess being from about 2 to 50 or more mole proportions relative to the first monomer. The second bifunctional monomer will react with the first monomer to provide a copolymeric material containing pendent groups extending from said copolymer which contain unreacted terminal functional moieties. The reactive groups of the bifunctional monomer are preferably separated by a chain containing from about 4 to about 10 carbon atoms, which also may be a cyclic as well as a straight chain. This second bifunctional monomer will also be added preferably in an aqueous solution, whereby the copolymer which is both entrapped and also absorbed in part in the pores of the inorganic support will be formed and from which pendent groups of the second monomer will extend. These pendent groups will contain unreacted terminal functional moieties due to the fact that a sufficient excess amount of the second bifunctional monomer was employed in treating the organic polymeric material originally absorbed on the support. The unreacted functional moieties are then available for covalent binding to the enzyme, which is added to the resulting organic-inorganic matrix, again usually in an aqueous solution. After removal of the unreacted materials by conventional means such as by treating, washing, etc., the enzyme covalently bound to the pendent functionalized groups remain attached at the terminal portions thereof.

Following this the long term stability and total activity of the immobilized enzyme is enhanced by treating the immobilized enzyme complex with an additional amount of the second bifunctional monomer in the presence of substrate if found to be beneficial. This treatment will result in the addition of more pendent groups to the complex thus resulting in increasing the number of binding sites for subsequent attachment of additional enzyme. Following treatment with the additional amount of the bifunctional monomeric material the excess material in then removed in a conventional manner and a substrate is then added to the complex. The addition of the substrate which is the substance to be converted is effected in order to protect the active sites of the complex from any possible deleterious effects which might occur from the other reagents or for any advantageous reason such as orientation of the enzyme molecule. Following the addition of the substrate to the complex which may be effected at relatively low temperatures ranging from about 0° to about 20° C., the complex is then treated with an additional amount of enzyme. The additional amount of enzyme will result in a greater amount of the enzyme being covalently bound to the excess pendent groups which are present as a result of the second addition of the bifunctional monomeric material.

Following the treatment of the complex with the additional amount of enzyme which is accompanied by periodic or continuous agitation, the excess reactants such as the substrate and unadsorbed and unreacted enzyme are again removed by conventional means followed by a washing of the complex with distilled water or suitable electrolyte or non-electrolyte solution. The final step of the process involves further treatment of the complex with a mixture of substrate and bifunctional monomeric material to effectively cross-link the pendent groups while protecting the active sites from any possible attack with the result of unwanted reactions. Again, the excess reagents are removed followed by washing of the final complex with appropriate solvent or solution. It is therefore readily apparent that the entire immobilization procedure can be conducted in a simple and inexpensive manner, for example, in a column packed with the inorganic supports, utilizing an aqueous or inexpensive solvent media, the procedure being conducted over a temperature differential which may range from subambient (about 5° C.) up to elevated temperatures of about 60° C., and preferably at ambient (about 20°-25° C.) temperature, said procedure being effected by utilizing a minimum of operating steps and, in addition, permitting a ready recovery of the excess reactants, unbound enzyme and finished composition of matter, of which the former may be reused.

In describing the preparation of the organic-inorganic supports of this invention I wish it understood that the terms "first" and "second" reactants are employed to clearly represent the operating procedure but are not to be considered as limiting in nature. Thus, the sequence of addition of those reactants may be reversed, if desired, particularly when the excess of the bifunctional monomer is in the lower part of the indicated range, although not necessarily with equivalent results.

Many of the inorganic supports reported in the prior art specify "controlled pore" materials such as glass, alumina, etc., having a pore diameter of from about 500 to 700 Angstroms for about 96% of the material and a maximum pore diameter of 1000 Angstroms, a surface area of about 40 to 70 m²/gm and about 40–80 mesh size particles. In addition, these supports may be coated with metallic oxides such as zirconium oxide and titanium oxide for greater stability. In contradistinction to these supports, it is contemplated within the scope of this invention that the inorganic porous supports which are utilized herein, will constitute materials which possess pore diameters ranging from about 100 Angstroms up to about 55,000 Angstroms. The surface area of the particular inorganic porous support will also vary over a relatively wide range, said range being from about 1 to about 500 m²/gm, the preferred range of surface area being from about 5 to about 400 m²/gm. The configuration of the inorganic porous support material will vary depending upon the particular type of support which is utilized. For example, the support material may be in spherical form, particulate form, as a ceramic monolith which may be coated with a porous inorganic oxide, etc., a membrane, ceramic fibers, alone or woven into a cloth, etc. The particle size may also vary over a wide range, again depending upon the particular type of support which is employed and also upon the substrate and the type of installation in which the enzyme conjugate is to be used. For example, if the support is in spherical form, the spheres may range in size from about 0.01" to about 0.25" in diameter, the preferred size ranging from about 1/32" to ⅛" in diameter, When the support is in particulate form, the particle size may also range between about the same limits. In terms of U.S. standard mesh sizes, such particles may range from about 2.5 to about 100 mesh, with about 10–80 mesh sizes preferred. Likewise, if the support is in the shape of ceramic fibers, the fibers may range from about 0.5 to about 20 microns in diameter or, if in the form of a membrane, the membrane may comprise a ceramic material which is cast into a thin sheet. It is to be understood that the aforementioned types of support configuration and size of the various supports are given merely for purposes of illustration, and it is not intended that the present invention be necessarily limited thereto.

It is also contemplated that the porous support material may be coated with various oxides of the type hereinbefore set forth or may have incorporated therein various other inorganic materials such as boron phosphate, etc., these inorganic materials imparting special properties to the support material. A particularly useful form of support will constitute a ceramic body which may have the type of porosity herein described for materials of the present invention or it may be honeycombed with connecting macrosize channels throughout, such materials being commonly known as monoliths, and which may be coated with various types of porous alumina, zirconia, etc. The use of such a type of support has the particular advantage of permitting the free flow of highly viscous substrates which are often encountered in commercial enzyme catalyzed reactions.

The inorganic porous support materials which are utilized as one component of the combined organic-inorganic matrix will include certain metal oxides such as alumina, and particularly gamma-alumina, silica, zirconia, silica-magnesia, silica-zirconia-alumina, etc., or gamma-alumina containing other inorganic compounds such as boron phosphate, etc., ceramic bodies, etc., as well as combinations of the aforementioned materials, one of said materials which may serve as a coating for another material comprising the support.

The copolymeric materials which are formed in situ in such a manner so that the copolymeric material is both entrapped and also absorbed in part in the pores of the inorganic support of the type hereinbefore set forth may be produced according to the general method hereinbefore described, that is, by first absorbing and/or adsorbing the support with a solution containing from about 2 to about 50% of a first bi- or multi-functional monomer which is preferably soluble in water or other solvents which are inert to the reactions subsequently employed. As hereinbefore set forth, it is then contemplated within the scope of this invention that a second monomer which is bi- or possibly multi-functional in nature is then added in similar manner in a solution, preferably aqueous in nature, to form an inorganic-organic matrix by further reaction with the first monomer adsorbed on and/or absorbed in the inorganic support to produce a copolymer which may also be cross-linked. The second bifunctional monomeric material is present in an excess as needed to produce pendent terminally functionalized groups in the range of from about 2 to about 50 moles or more of second bifunctional monomeric material per mole of first monomer. The amount of the first monomer which is absorbed in or adsorbed on the support will depend upon many variations which include the type of porous support, the pH of the solution in which it is dissolved, the concentration of the material which is present as well as other reaction parameters including temperature, pressure, etc. While the excess of the second bifunctional monomeric material may range from about 2 to about 50 moles or more per mole of first monomer, it is usually satisfactory that the excess be in the range of from about 4 to about 25 moles of bifunctional monomer. The unreacted excess monomer may be readily recovered for reuse as well as the unabsorbed first monomer originally added to the support.

The functional groups which are present on the bifunctional monomeric material will comprise well-known reactive moieties such as amino, hydroxyl, carboxyl, thiol, carbonyl, etc., moieties. As was also hereinbefore set forth, the reactive groups which are present on the bifunctional monomers are preferably, but not necessarily, separated by chains containing from about 4 to about 10 carbon atoms. The aforesaid reactive moieties are capable of covalently bonding with both the initial additives and subsequently, after washing out unreacted materials, with the enzyme which should be added in a subsequent step, said enzyme being then covalently bound to the functional group at the terminal portion of the pendent chain. After addition of the enzyme to this composition, followed by the subsequent steps of treatment with additional second bifunctional monomer and enzyme in the presence of a substrate which will protect the active sites of the immobilized enzyme complex, produce an enzyme conjugate which possesses excellent long term stability and total activity properties.

Some specific examples of first monomeric materials which may be initially absorbed on the inorganic support will include water soluble polyamines such as ethylenediamine, diethylenetriamine, triethylenetetramine, tetraethylenepentamine, pentaethylenehexamine, hexamethylenediamine, polyethyleneimine, etc.; water insoluble but solvent or aqueous acid soluble polyamines such as methylenedicyclohexylamine, methylenedianiline, etc., and natural and synthetic, partially hydrolyzed polymers and preformed polymers, soluble in either aqueous or solvent media, such as partially hydrolyzed Nylon, collagen, polyacrolein, polymaleic anhydride, alginic acid, casein hydrolysate, gelatin, etc. Some specific examples of intermediate bifunctional monomeric materials which may be added to the above enumerated products in an excess in the range hereinbefore set forth to produce an organic-inorganic matrix and which possess the necessary characteristics hereinbefore set forth include compounds such as glutaraldehyde, adipoyl chloride, sebacoyl chloride, toluenediisocyanate, hexamethylenediisocyanate, terephthalic diesters or acyl halides, etc. Due to the large excess of intermediary, or spacer, bifunctional monomeric molecules which are used, the polymeric matrix which is formed will contain pendent groups comprising the spacer molecules, said molecules extending from the matrix and having reactive moieties available at the terminal portions thereof which are capable of reacting with and binding the enzyme to the spacer molecules via covalent bonds. Therefore, it is readily apparent that a suitable organic-inorganic matrix which is applicable in many situations will be formed with the support material by adsorbing and/or absorbing any of the type of materials hereinbefore described which are known to the art and then treated with any bifunctional monomer molecule which is also known to the art and is suitably functionalized to react with the original additive, provided that a large enough excess of the bifunctional molecule is used to provide pendent groups which are capable of subsequently reacting with the enzyme which is desired to be immobilized. By utilizing these functional pendent groups as a binding site for the enzymes, it will permit the enzymes to have a greater mobility and thus permit the catalytic activity of the enzyme to remain at a high level for a relatively longer period of time than will be attained when the enzyme has been immobilized by any of the other methods such as entrapment in a gel lattice, adsorption on a solid surface or cross-linkage of the enzyme with adjacent enzyme molecules by means of bifunctional reagents, etc. Not all formulations, however, will produce equivalent results in terms of stability or activity.

Examples of enzymes which may be immobilized by a covalent bonding reaction and which contain an amino group capable of reacting with an aldehydic, isocyanato, acyl, ester, etc., moiety of the pendent group which is attached to a polymeric material entrapped and also adsorbed in part in the pores of a porous support material will include trypsin, papain, hexokinase, beta-galactosidase (lactase), ficin, bromelain, lactate dehydrogenase, glucoamylase, chymotrypsin, pronase, glucose isomerase, acylase, invertase, amylase, glucose oxidase, pepsin, rennin, protease, xylanase, cellulase, etc. In general any enzyme whose active site is not involved in the covalent bonding can be used although not necessarily with equivalent results. While the aforementioned discussion was centered about pendent groups which contain as a functional moiety thereon an aldehydic or isocyanato group, it is also contemplated within the scope of this invention that the pendent group can contain other functional moieties capable of reaction with carboxyl, sulfhydryl or other moieties usually present in enzymes. However, the covalent bonding of enzymes containing these other moieties with other pendent groups may not necessarily be effected with equivalent results and may also involve appreciably greater costs in preparing intermediates. It is to be understood that the aforementioned listing of porous solid supports, monomers, hydrolysates, polymers and enzymes are only representative of the various classes of compounds which may be used, and that the present invention is not necessarily limited thereto.

The preparation of the compositions of matter of the present invention is preferably effected in a batch type operation as heretofore already described in detail, although it is also contemplated within the scope of this invention that the formation of the finished composition of matter may also be effected in a continuous manner of operation. When a continuous type operation is used, a quantity of the porous solid support material is placed in an appropriate apparatus, usually constituting a column. The porous solid support material may be in any form desired such as powder, pellets, monoliths, etc., and is charged to the column, after which a preferably aqueous solution of, for example, a polyfunctional amine is contacted with the porous support until the latter is saturated with the amine solution and the excess is then drained. An intermediary spacer such as a reactive bifunctional monomer molecule such as glutaraldehyde is then contacted with the saturated support, said bifunctional molecule being present in an excess in the range of from about 2 to about 50 moles or more per mole of polyfunctional amine, as hereinbefore set forth. The formation of the copolymeric matrix is thus effected in an aqueous system, said reaction being effected during a period of time which may range from about 1 to about 10 hours or more in duration, but is usually of short duration. Following the completion of the desired residence time the excess glutaraldehyde is removed by draining and washing out any water soluble and unreacted materials, which in the case of a polyamine is preferably done with a buffer solution possessing a pH of about 4, although distilled water is usually found to be satisfactory.

To form an immobilized enzyme conjugate an aqueous solution of an enzyme of the type hereinbefore set forth in greater detail is contacted or recycled through the column thereby effecting a covalent bonding of the enzyme to the terminal aldehydic groups of the functionalized pendent moieties which extend from the matrix. This occurs until there is no further covalent binding of the enzyme to the pendent molecules. Following this a substrate such as glucose or fructose if the enzyme is to be utilized in converting said substrate is then cycled through the column followed by the addition of the reactive bifunctional monomer, the addition of the substrate and the bifunctional monomer acting (1) to protect (if need be) the active sites of the enzyme and (2) adding additional monomer to the complex whereby further pendent groups with reactive moieties supported at the terminal portions thereof are rendered available for additional enzyme bonding. After passage of the substrate and bifunctional monomer through the column, the column is then drained and the treated enzyme matrix complex is washed to remove any excess substrate and monomer still present. After passage of the wash water through the column, an additional amount of the particular enzyme utilized is recycled through the column to afford additional covalent bonding to the aforesaid functional moieties of the pendent groups of the bifunctional monomer. The excess enzyme is recovered in the effluent after draining and the covalently bound enzyme-support matrix complex is then further treated with an additional amount of substrate and bifunctional monomer, the latter acting to cross-link any available pendent groups while the substrate again protects the active sites of the complex. After washing the complex the column is thus ready for use in chemical reactions in which the catalytic effect of the enzyme is to take place. The aforesaid procedures are, for the most part, conducted within the time, temperature and concentration parameters hereinbefore described in the batch type procedure and will result in comparable immobilized enzyme complexes which possess increased stability and activity over complexes which have not been subjected to the particular steps of the process set forth. It is also contemplated within the scope of this invention that with suitable modifications of pH and temperature parameters which will be obvous to those skilled in the art, the process may be applied to a wide variety of inorganic porous supports, polymer forming reactants or monomers and enzymes.

The following examples are given for purposes of illustration of the improved stability and activity of immobilized enzyme complexes which have been prepared according to the process hereinbefore set forth. However, these examples are given merely for purposes of illustration and it is to be understood that the present invention is not necessarily limited thereto.

EXAMPLE I

In this example, 1.5 grams of porous gamma-alumina having a particle size of 60–80 mesh, a pore diameter ranging from about 300 to 2000 Angstroms and a surface area of about 150 $m^2/g$ was treated with 7.5 ml of a 5% aqueous solution of polyethyleneimine. The treatment was effected under vacuum for a period of about 45 minutes to remove entrapped air and to facilitate the penetration of the solution into the pores of the support. The excess polyethyleneimine solution was decanted by use of a filter stick and the treated support was washed with 1.5 ml of distilled water. Following this 5 ml of 2.5% aqueous glutaraldehyde solution was added at ambient temperature and allowed to react for a period up to 1.5 hours with occasional stirring. The excess glutaraldehyde was then decanted and the inorganic-organic complex was washed 10 times with 20 ml of distilled water to remove unreacted and unabsorbed reagents.

The support matrix prepared according to the above paragraph was treated with 4.2 ml of a solution containing 2000 International Units of glucose isomerase and buffered, utilizing 0.04 mole of a phosphate buffer which possessed a pH of 7.4. The covalent bonding of the enzyme was allowed to proceed with periodic agitation for a period of 48 hours while maintaining the temperature in a range of from 2° to 6° C. At the end of this period the excess glucose isomerase solution was decanted and the immobilized enzyme conjugate was washed with water to remove any unbound and/or unabsorbed enzyme.

The conjugate was then placed in a suitable column and assayed for activity by the continuous flow technique with a 45% aqueous fructose solution at a temperature of 60° C. The assay disclosed that the immobilized enzyme possessed 850–950 International Units of activity per gram. In addition the half-life as measured in a differential reactor ranged from 18 to 22 days.

EXAMPLE II

To illustrate the improved long range stability and increase activity of an immobilized enzyme complex which is prepared according to the process of this invention, the complex which was prepared according to the method set forth in Example I above was treated with 3 ml of a buffered fructose solution having a final concentration of approximately 30%. To this mixture was added an aqueous solution of glutaraldehyde to a final concentration of about 0.7%. The mixture was allowed to stand for a period of 30 minutes at room temperature while intermittently agitating the mixture. At the end of this 30 minute period the excess reactants were removed by decantation and the immobilized enzyme complex was washed 10 to 15 times with 60 ml of distilled water. To this immobilized enzyme complex was then added 1400 units of glucose isomerase and the mix was allowed to sit, with periodic agitation, for 48 hours. At the end of this period excess enzyme was decanted.

Following this the conjugate was then placed in a suitable column and assayed for activity utilizing a continuous flow technique with a 45% aqueous fructose solution plus $MgSO_4$, said reaction taking place at a temperature of 60° C. It was determined by assay that the activity of the immobilized enzyme was 1500 International Units/gram with a half-life as measured in a differential reactor ranging from 27.7 to 31.1 days.

EXAMPLE III

The immobilized enzyme conjugate as prepared in Example II above was then further treated with a solution containing 30% concentration of buffered glucose or fructose and 0.7% concentration of glutaraldehyde for a period of 30 minutes. The reaction was effected at room temperature with intermittent agitation of the mixture to insure a complete contact of the solution with an immobilized enzyme complex. At the end of the 30 minute period the excess reagents were again removed by decantation and the complex washed 10 to 15 times with 60 ml of distilled water.

As in the above two examples, the final immobilized enzyme complex was again assayed for activity utilizing a continuous flow technique utilizing a 45% aqueous fructose solution plus $MgSO_4$ at a temperature of 60° C. The assay of this solution disclosed that the activity of the immobilized glucose isomerase was now in excess of 1600 International Units/gram and possessed a half-life ranging from 31.0 to 34.9 days.

It is apparent from a comparison of the above examples that the immobilized glucose isomerase which was treated with additional cross-linking agents, enzymes, utilizing a substrate medium to protect the active sites of the immobilized enzyme complex resulted in a complex which possessed an activity which was approximately twice as great as that which was possessed by an immobilized enzyme complex prepared without post-treatment while the stability as measured for the half-life of the complexes was almost twice as long for the post-treated immobilized enzyme complex when compared to the immobilized enzyme complex which was not subjected to post-treatment in the manner hereinbefore set forth.

I claim as my invention:

1. A process for increasing the activity and stability of an immobilized enzyme which comprises the steps of:
   (a) treating an inorganic porous support material which possesses pore diameters of from about 100 to about 55,000 Angstroms and a surface area of from about 1 to about 500 $m^2/g$ with a solution of a first water soluble bifunctional monomer;
   (b) removing unadsorbed monomer;
   (c) contacting the treated support material with a solution containing an excess of a second bifunctional monomeric material of from about 2 to about 50 moles of said bifunctional monomer per mole of said first water soluble bifunctional monomer wherein said second bifunctional monomeric material reacts with said first bifunctional monomer adsorbed on said support material to form a polymeric material and to provide pendent terminally functionalized groups for convalent bonding thereto of an enzyme;
   (d) removing unreacted bifunctional monomeric material;

(e) treating the resultant inorganic-organic support matrix with an enzyme to covalently bind said enzyme to said support matrix;

(f) treating the resultant immobilized enzyme-support matrix complex with an additional amount of said second bifunctional monomeric material to provide pendent terminally functionalized groups for covalent bonding thereto of additional enzymes;

(g) removing excess bifunctional monomeric material;

(h) adding a substrate for said enzyme to the complex;

(i) treating said complex with an additional amount of said enzyme at a temperature in the range of from about 0° to about 20° C.;

(j) removing excess substrate and enzyme; and, (k) treating said complex with a mixture of said substrate and bifunctional monomeric material.

2. The process as set forth in claim 1 in which said monomeric porous support material is alumina.

3. The process as set forth in claim 2 in which said alumina is gamma-alumina.

4. The process as set forth in claim 1 in which said inorganic porous support material is silica.

5. The process as set forth in claim 1 in which said inorganic porous support material is silica-alumina.

6. The process as set forth in claim 1 in which said first monomer is polyethyleneimine.

7. The process as set forth in claim 1 in which said first monomer is tetraethylenepentamine.

8. The process as set forth in claim 1 in which said second bifunctional monomeric material is glutaraldehyde.

9. The process as set forth in claim 1 in which said second bifunctional monomeric material is toluene diisocyanate.

10. The process as set forth in claim 1 in which said enzyme is glucose isomerase.

11. The process as set forth in claim 1 in which said enzyme is glucose oxidase.

12. The process as set forth in claim 1 in which said enzyme is glucoamylase.

13. The process as set forth in claim 1 in which said enzyme is lactase.

14. The process as set forth in claim 1 in which said substrate is glucose.

15. The process as set forth in claim 1 in which said substrate is fructose.

* * * * *